US00PP21874P2

(12) United States Plant Patent
Kapusta

(10) Patent No.: US PP21,874 P2
(45) Date of Patent: Apr. 19, 2011

(54) ***LONICERA* PLANT NAMED 'INOV71'**

(50) Latin Name: *Lonicera periclymenum*
Varietal Denomination: Inov71

(75) Inventor: Véronique Kapusta, Beaucouzé (FR)

(73) Assignees: Institut National de la Recherche Agronomique, Paris (FR), part interest; Saphinon S.N.C., Beaufort (FR), part interest ( * ) Notice: Subject to any disclaimer, the term of this patent is extended or adjusted under 35 U.S.C. 154(b) by 0 days.

(21) Appl. No.: 12/584,237

(22) Filed: Sep. 2, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner* — June Hwu
(74) *Attorney, Agent, or Firm* — Penny J. Aguirre

(57) ABSTRACT

A new cultivar of *Lonicera*, 'Inov71', characterized by its columnar and compact plant habit with erect stems, its resistance to powdery mildew, black spot, and its fragrant inflorescences that are present in June and July that emerge white in color with purple-red markings and turn creamy yellow as they mature.

2 Drawing Sheets

Botanical classification: *Lonicera pericylmenum.*
Variety denomination: 'Inov71'.

RELATED APPLICATIONS

This application is co-pending with a U.S. Plant Patent application for a cultivar discovered from similar parentage entitled *Lonicera* Plant Named 'Inov86' (U.S. patent application Ser. No. 12/584,231).

BACKGROUND OF THE INVENTION

The present invention relates to a new and distinct cultivar of *Lonicera periclymenum* and will be referred to hereafter by its cultivar name, 'Inov71'. 'Inov71' is a new cultivar of honeysuckle, a vine grown for use as an ornamental landscape plant.

The new Invention arose from an ongoing controlled breeding program by the Inventor in Beaucouzé, France. 'Inov71' originated as a seedling of *Lonicera periclymenum* 'Florida' (not patented, syns. *Lonicera periclymenum* 'Serotina Florida' and *Lonicera periclymenum* var. *serotina* 'Florida') that had been obtained by irradiated by gamma ray irradiation at a level of 30Gy in the Inventor's laboratory in summer of 1996. The male parent is unknown but is thought that 'Inov71' results from self-pollination. The new cultivar was selected as a single unique plant in 2001.

Asexual reproduction of the new cultivar was first accomplished by the Inventor using softwood stem cuttings in 2001 in Beaucouzé, France. The characteristics of this cultivar have been determined to be stable and are reproduced true to type in successive generations.

SUMMARY OF THE INVENTION

The following traits have been repeatedly observed and represent the characteristics of the new cultivar as grown outdoors in a field plot for eight years in Beaucouzé, France. These attributes in combination distinguish 'Inov71' as a unique cultivar of *Lonicera.*

1. 'Inov71' exhibits a columnar plant habit with erect stems.
2. 'Inov71' exhibits a compact plant habit.
3. 'Inov71' exhibits resistance to powdery mildew and black spot disease.
4. 'Inov71' blooms in June and July with fragrant flowers that emerge white in color with purple-red markings and turn to a creamy yellow color as they mature.

In comparison to the female parent plant (and probable male parent), 'Florida', 'Inov71' differs in having a columnar and more compact plant habit. In comparison to typical plants of the species, 'Inov71' differs in being less vigorous, in having a much more compact habit, and in being earlier flowering. 'Inov71' is similar in disease and green fly resistance to its sister seedling, 'Inov86', however 'Inov71' has smaller flowers and inflorescences and a more columnar habit. 'Inov71' can also be compared to the cultivars 'Scentsation' (U.S. Plant Pat. No. 16,240) and 'Graham Thomas' (not patented), which are similar in having abundant, fragrant flowers, however 'Inov71' can also be distinguished from these cultivars in having a more compact and columnar plant habit.

BRIEF DESCRIPTION OF THE DRAWING

The accompanying colored photographs were taken in mid summer and illustrate the overall appearance and distinct characteristics of a 6 year-old plant the new *Lonicera* as grown in a trial garden in Beaucouzé, France.

The photograph in FIG. 1 provides an overall view of the abundance of blooms and the columnar and compact plant habit of 'Inov71'.

Figure 1:
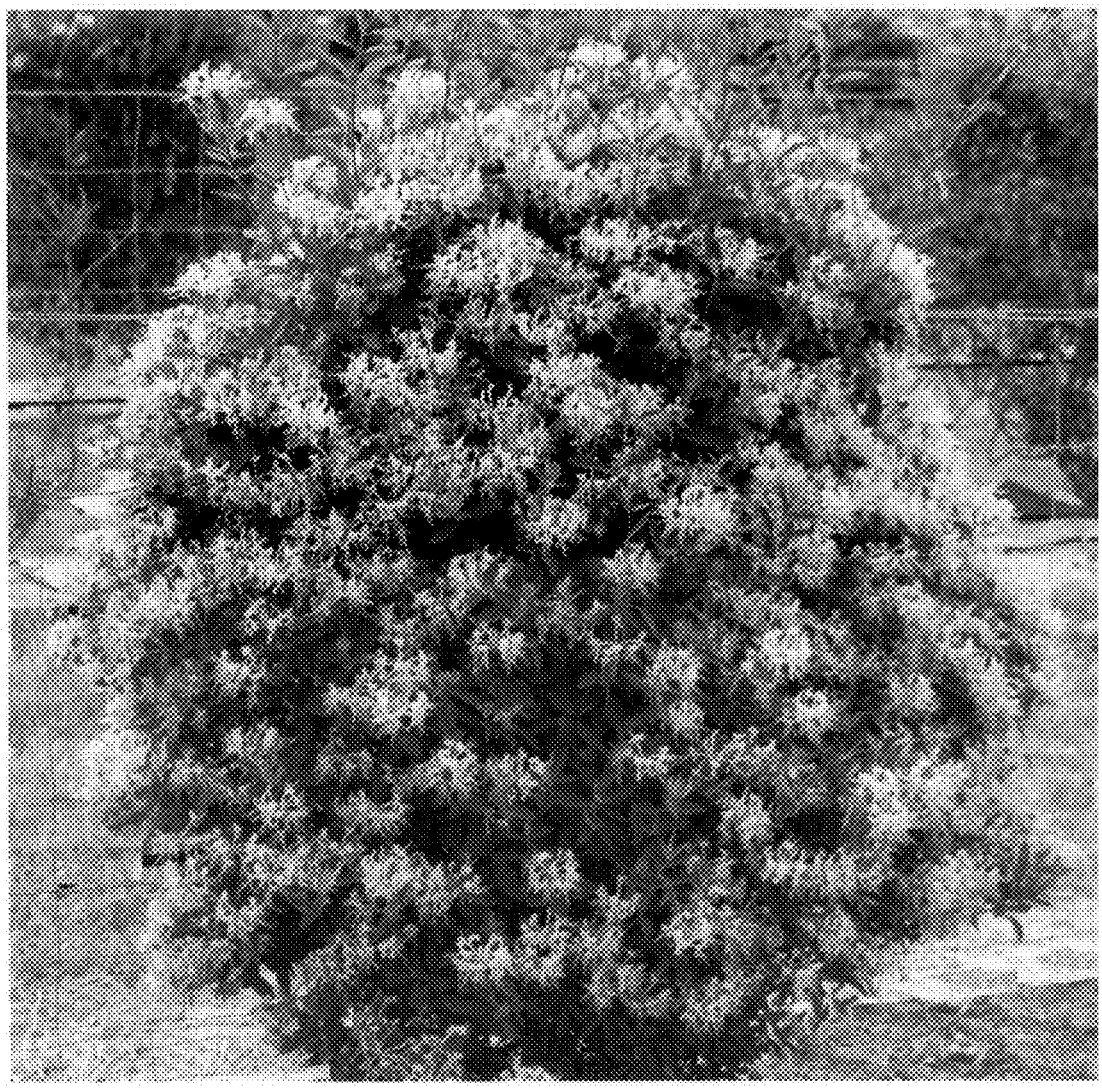
Figure 2:
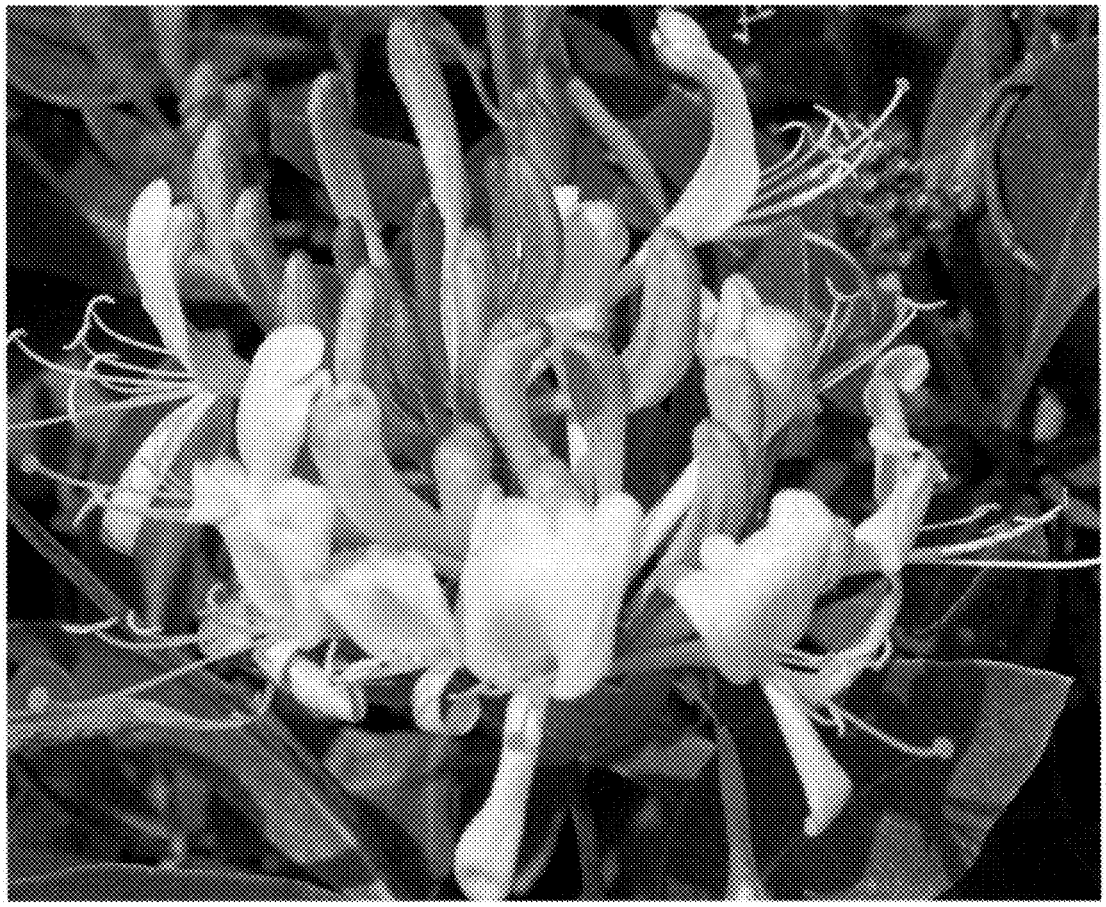

The photograph in FIG. 2 provides a close-up view of an inflorescence of 'Inov71'.

The colors in the photographs may differ slightly from the color values cited in the detailed botanical description, which accurately describe the colors of the new *Lonicera.*

DETAILED BOTANICAL DESCRIPTION

The following is a detailed description of a 6 year-old plant the new *Lonicera* as grown in a trial field in Beaucouzé, France. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Botanical classification.*—*Lonicera periclymenum* 'Inov71'.

*Parentage.*—Gamma irradiation of *Lonicera periclymenum* 'Florida' seedling.

*Blooming period.*—Blooms from early summer until Frost in Beaucouzé, France.

*Plant habit.*—Columnar and compact vine with erect stems.

*Plant size.*—Reaches 2 to 3 m in height and 1 to 1.5 m in width.

*Diseases and pests.*—Has shown good resistance to powdery mildew and black spot.

*Hardiness.*—U.S.D.A. Zones 4 to 8.

*Root description.*—Fibrous.

Growth and propagation:

*Propagation.*—Terminal, softwood stem cuttings.

*Growth rate.*—Moderate.

Stem description:

*Shape.*—Round.

*Stem color.*—New growth; 144B heavily overlaid with 187A and 187B, mature wood and bark 177A.

*Stem size.*—Old wood; ranges about 2.5 cm in diameter near base to 4 mm in diameter on lateral branches, new growth; average of 2 mm in diameter, up to 3 m in length.

*Stem surface.*—New growth; Glabrous, mature wood is dull and smooth and becoming bark-like as it ages.

*Internode length.*—Average of 1.7 cm.

*Branching.*—Well branched with new growth emerging in opposite arrangement from axillary nodes.

Foliage description:

*Leaf shape.*—Elliptic.

*Leaf division.*—Simple.

*Leaf base.*—Cuneate.

*Leaf apex.*—Acute to attenuate.

*Leaf fragrance.*—None.

*Leaf venation.*—Pinnate, only mid rib is conspicuous, color on upper surface, 144C, color on lower surface; 183B.

*Leaf margins.*—Entire.

*Leaf arrangement.*—Opposite.

*Leaf attachment.*—Petiolate.

*Leaf surface.*—Glabrous on upper surface and lower surface.

*Leaf internode length.*—Average of 1.7 cm.

*Leaf size.*—Average of 5 cm in length and 2.5 cm in width.

*Leaf color.*—Newly expanded leaves upper surface; ranges from 144A to 144B, newly expanded leaves lower surface; 138B, mature leaves upper surface; ranges from 137A to 137B, mature leaves lower surface; ranges from 138A to 138B.

*Petioles.*—Average of 6 mm in length and 2 mm in width, 144D in color, glabrous surface.

*Stipules.*—None.

Inflorescence description:

*Inflorescence type.*—Comprised whorls (contracted corymb) of tubular flowers at terminus of lateral branches with sometime with smaller inflorescences on upper auxiliary nodes.

*Inflorescence size.*—Ranges from 3.5 to 4 cm in height and 7 to 8 cm in width.

*Flower buds.*—Oblanceolate in shape, 155A in color with longitudinal stripes and shading of 63A and 64A, ranges from 3.8 to 4.2 cm in length, average of 6 mm in width.

*Flower fragrance.*—Fragrant.

*Lastingness of inflorescence.*—Inflorescence blooms for 2 to 3 weeks with individual flowers lasting about 4 days, lower whorls begin opening first, self-cleaning.

*Flower quantity.*—18 to 24 flowers per inflorescence.

*Flower type.*—Tubular, 2-lipped.

*Flower aspect.*—Outward.

*Flower size.*—Average of 1.4 cm in diameter and 4 cm in depth.

*Peduncles.*—None, sessile to stem.

*Bracts.*—None observed.

*Pedicels.*—None, sessile to stem.

*Calyx.*—5-starred, inconspicuous, about 1 mm in diameter and depth.

*Sepals.*—5, un-fused portion in triangular acute tip, fused base, 145C in color, entire margin on tips, glabrous surface.

*Petals.*—5, fused to tube at base, tube portion is an average of 2.4 cm in length and 4 mm in width, free portion is 2-lipped with upper lip comprised of 4 fused petals flared outward to reflexed and lower lip comprised of 1 petal that is reflexed, free portion of fused petals are about 1.4 cm in length and in width together, free portion of upper lip petals are triangular in shape and about 4 mm in length and width, free portion of lower lip petal is oblong in shape and about 5 cm in length and 4 mm in width, all free petals portions have a rounded apex and entire margin, outer and inner surface is glabrous, color of inner surface (free portions and tube); 155A when opening and 155A with longitudinal stripes of 63A and 63A when fully open, color of outer surface (free portions and tube); 158A and 158B when opening and 158C with longitudinal stripes of 64C when fully open, color of both surfaces when fading; 20C and 20B.

Reproductive organs:

*Gynoecium.*—1 pistil, an average of 4.3 cm in length and exserted beyond corolla, style is about 4.1 cm in length, and 155A in color, stigma is about 2 mm in diameter and 0.7 mm in depth, flattened globose in shape and 160C in color, ovary is inferior, ovoid in shape and ranges from 145A to 144C in color.

*Androcoecium.*—5 stamens, about 3.5 cm in length and exserted beyond corolla, filaments are 155A in color, about 3.3 cm in length, anthers are about 4 mm in length, dorsifixed, 24B in color when flower is fully open, pollen is abundant in quantity and 24B in color.

*Fruit and seed.*—True berry, round in shape, about 1 cm in diameter, 44A in color.

It is claimed:

1. A new and distinct cultivar of *Lonicera* plant named 'Inov71' as herein illustrated and described.

* * * * *